(12) United States Patent
Niizuma et al.

(10) Patent No.: US 11,573,197 B2
(45) Date of Patent: Feb. 7, 2023

(54) GAS SENSOR WITH ANGLED SEALING ELEMENT

(71) Applicant: NGK INSULATORS, LTD., Aichi (JP)

(72) Inventors: Shotaro Niizuma, Kasugai (JP);
Yusuke Watanabe, Nagoya (JP);
Toshihiro Hirakawa, Kasugai (JP);
Hayami Aota, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 64 days.

(21) Appl. No.: 17/172,104

(22) Filed: Feb. 10, 2021

(65) Prior Publication Data
US 2021/0247355 A1    Aug. 12, 2021

(30) Foreign Application Priority Data
Feb. 12, 2020    (JP) .............................. JP2020-021150

(51) Int. Cl.
*G01N 27/407*      (2006.01)
*G01N 33/00*      (2006.01)

(52) U.S. Cl.
CPC ..... *G01N 27/4078* (2013.01); *G01N 27/4077* (2013.01); *G01N 33/0037* (2013.01); *Y02A 50/20* (2018.01)

(58) Field of Classification Search
CPC .......... G01N 27/4078; G01N 27/4077; G01N 33/0037; Y02A 50/20
See application file for complete search history.

(56) References Cited

U.S. PATENT DOCUMENTS

| | | | |
|---|---|---|---|
| 2001/0023612 A1 | 9/2001 | Kojima | |
| 2002/0017128 A1 | 2/2002 | Shirai | |
| 2003/0024300 A1 | 2/2003 | Kojima | |
| 2005/0241368 A1* | 11/2005 | Yamauchi | G01N 27/4078 73/31.05 |
| 2006/0162422 A1* | 7/2006 | Geier | G01N 27/407 73/23.31 |
| 2012/0031171 A1* | 2/2012 | Masuda | G01N 27/4062 73/31.05 |
| 2017/0276638 A1 | 9/2017 | Isaka et al. | |

FOREIGN PATENT DOCUMENTS

| | | |
|---|---|---|
| JP | 3800978 B2 | 7/2006 |
| JP | 4576722 B2 | 11/2010 |
| JP | 4670197 B2 | 4/2011 |
| JP | 2017-173221 A | 9/2017 |
| JP | 6493133 B2 | 4/2019 |

* cited by examiner

*Primary Examiner* — Randy W Gibson
*Assistant Examiner* — John M Royston
(74) *Attorney, Agent, or Firm* — Mattingly & Malur, PC

(57) ABSTRACT

A gas sensor includes a sensor element, a tubular body made of metal, and a sealing material. The sensor element has a surface. The tubular body has a through hole which is formed along the axial direction and through which the sensor element is inserted. The sealing material is placed inside the through hole and between the inner peripheral surface of the through hole and the sensor element. The sealing material covers a part of the surface of the sensor element. When the sensor element is viewed in cross section from a second direction perpendicular to a first direction corresponding to the longitudinal direction of the sensor element, the sealing material forms a first inclination angle of not less than 10° and not more than 80° with respect to the surface.

8 Claims, 11 Drawing Sheets

FIG. 10

【TABLE】

| | CONDITION OF END SURFACE OF FILLER | ANGLE OF INCLINATION $\theta_1$ [°] | EVALUATION |
|---|---|---|---|
| EXAMPLE 1 | (1) FIG. 3A (STRAIGHT LINE L1) | 80 | B |
| EXAMPLE 2 | | 70 | A |
| EXAMPLE 3 | | 50 | A |
| EXAMPLE 4 | | 20 | A |
| EXAMPLE 5 | (2) FIG. 3B (STRAIGHT LINES L1, L2) | 80 | B |
| EXAMPLE 6 | | 70 | A |
| EXAMPLE 7 | | 30 | A |
| EXAMPLE 8 | | 10 | A |
| EXAMPLE 9 | (3) FIG. 5A (CURVED LINE L1) | 80 | B |
| EXAMPLE 10 | | 70 | A |
| EXAMPLE 11 | | 50 | A |
| EXAMPLE 12 | | 20 | A |
| EXAMPLE 13 | (4) FIG. 5B (CURVED LINES L1, L2) | 80 | B |
| EXAMPLE 14 | | 70 | A |
| EXAMPLE 15 | | 30 | A |
| EXAMPLE 16 | | 10 | A |
| COMPARATIVE EXAMPLE 1 | (1) FIG. 3A (STRAIGHT LINE L1) | 90 | C |

GAS SENSOR WITH ANGLED SEALING ELEMENT

CROSS-REFERENCE TO RELATED APPLICATION

This application is based upon and claims the benefit of priority from Japanese Patent Application No. 2020-021150 filed on Feb. 12, 2020, the contents of which are incorporated herein by reference.

BACKGROUND OF THE INVENTION

Field of the Invention

The present invention relates to a gas sensor for measuring the concentration of gas.

Description of the Related Art

Japanese Laid-Open Patent Publication No. 2017-173221 discloses a gas sensor that uses ceramic supporters and powder compacts as sealing material to seal the sensor element within a housing. The sealing material has a through hole and covers the sensor element. By gas-tightly sealing the sensor element, measured gas and reference gas are separated so that the measured gas can be measured accurately.

SUMMARY OF THE INVENTION

Now, the end of the sealing material (located at an opening of the through hole) is ordinarily in contact with the surfaces of the sensor element at right angles. Accordingly, if an impact (stress) is applied to the gas sensor, the stress is likely to concentrate especially at the end of the sealing material and its vicinity. This will make it difficult to keep the gas-tightness of the gas sensor and hence lower the measuring accuracy.

The present invention has been devised considering such a problem and an object of the invention is to provide a gas sensor capable of reducing deterioration of gas-tightness due to impact.

A gas sensor according to an aspect of the invention includes: a sensor element; a tubular body made of metal and including a through hole which is formed along an axial direction and through which the sensor element is inserted; and a sealing material placed inside the through hole and between an inner peripheral surface of the through hole and the sensor element, the sealing material covering a part of a surface of the sensor element and including an end surface, wherein, when the sensor element is viewed in cross section from a second direction that is perpendicular to a first direction corresponding to a longitudinal direction of the sensor element, the end surface forms a first inclination angle of not less than 10° and not more than 80° with respect to the surface.

According to the present invention, it is possible to reduce deterioration of gas-tightness due to impact.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 10 is a table showing the results of evaluation; and

DESCRIPTION OF THE PREFERRED EMBODIMENTS

The gas sensor according to the present invention will be described below in detail in connection with preferred embodiments while referring to the accompanying drawings.

Figure 1:
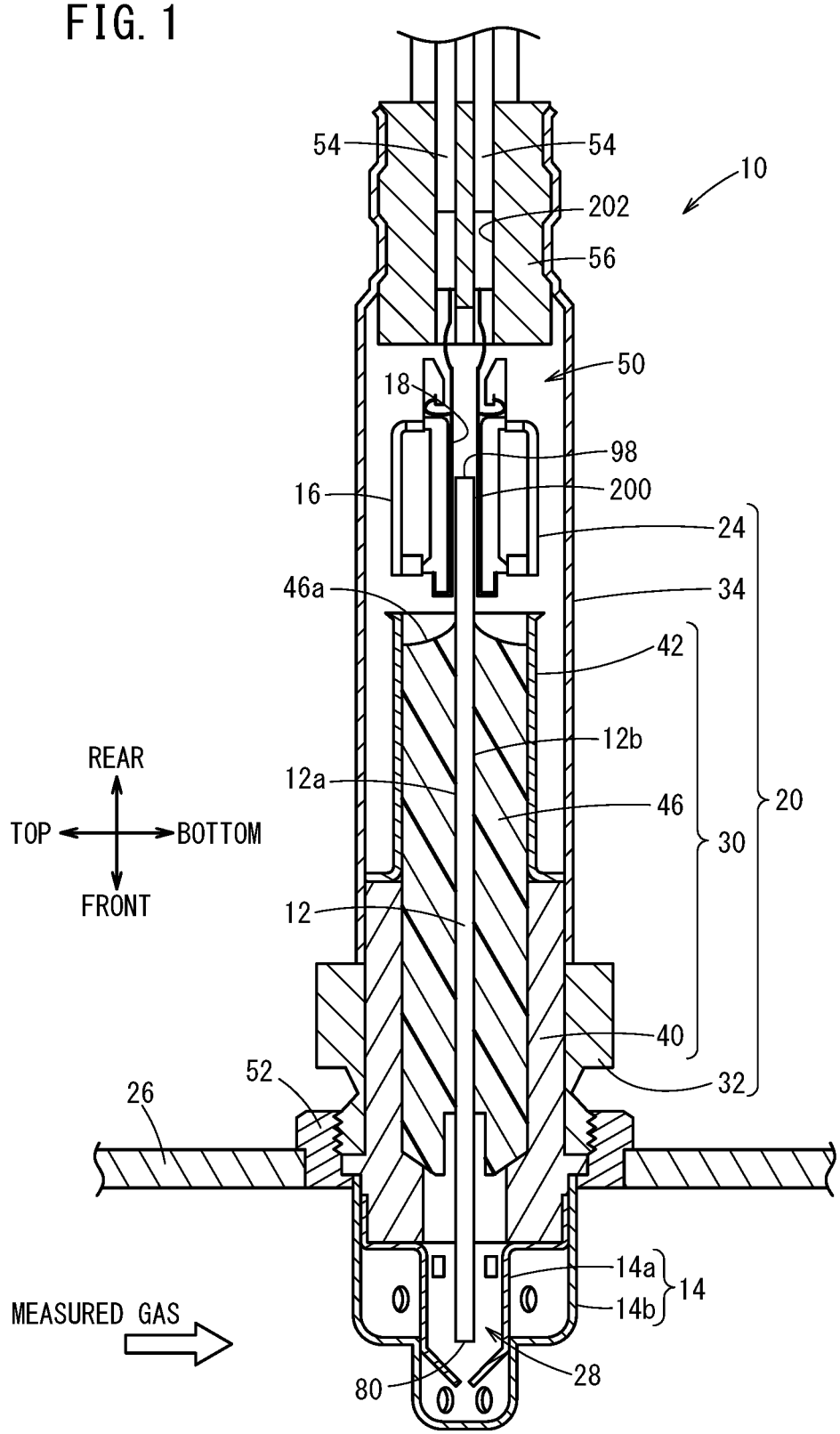
FIG. 1 is a cross section of a gas sensor according to an embodiment.

As shown in FIG. 1, a gas sensor 10 according to this embodiment includes a sensor element 12. The sensor element 12 has an elongated cuboidal shape. The longitudinal direction of the sensor element 12 (the left-right direction in FIG. 2) is defined as a front-rear direction (an example of a first direction in which the sensor element 12 extends), and the thickness direction of the sensor element 12 (the top-bottom direction in FIG. 2) is defined as a top-bottom direction (an example of a third direction that is perpendicular to main surfaces (surfaces) 12a, 12b of the sensor element 12 described later). The width direction of the sensor element 12 (a direction perpendicular to the front-rear and top-bottom directions) is defined as a left-right direction.

As shown in FIG. 1, the gas sensor 10 includes the sensor element 12, a protective cover 14 for protecting the front end of the sensor element 12, and a sensor assembly 20 including a ceramic housing 16. The ceramic housing 16 holds a rear end portion of the sensor element 12, and functions as a connector 24 by terminal members 18 electrically connected to the sensor element 12 being attached thereto.

As shown in the drawing, the gas sensor 10 is attached to a pipe 26 such as an exhaust gas pipe of a vehicle, for example, and used to measure concentrations of specific gases such as NOx, $O_2$, etc. that are contained in the exhaust gas as a measured gas.

The protective cover 14 includes a bottomed-tube-like inner protective cover 14a covering the front end of the sensor element 12, and a bottomed-tube-like outer protective cover 14b covering the inner protective cover 14a. The inner protective cover 14a and the outer protective cover 14b have formed therein a plurality of holes through which the measured gas can flow into the interior of the protective cover 14. A sensor element cavity 28 is formed as a space enclosed by the inner protective cover 14a, and the front end of the sensor element 12 is disposed within the sensor element cavity 28.

The sensor assembly 20 includes an element seal body 30 for sealing and fixing the sensor element 12, a nut 32 attached to the element seal body 30, an outer tube 34, and the connector 24 that is in contact with and electrically connected to electrodes (not shown) that are formed on the surfaces (top and bottom surfaces) of the sensor element 12 in the rear part thereof.

The element seal body 30 includes a tubular main fitting 40, a tubular, inner tube 42 (an example of a tubular body made of metal) that is fixed by welding coaxially with the main fitting 40, and a sealing material 46 sealed in a through hole in the interior of the main fitting 40 and the inner tube 42. The sensor element 12 is located on the center axis of the element seal body 30 and passes through the element seal body 30 along the front-rear direction.

The nut 32 is fixed coaxially with the main fitting 40, and has a male thread portion formed on its outer peripheral surface. The male thread portion of the nut 32 is inserted in a fixing member 52 that is welded to the pipe 26 and has a female thread formed on its inner peripheral surface. The gas sensor 10 is thus fixed to the pipe 26 with the front end of the sensor element 12 and the protective cover 14 projecting in the pipe 26.

The outer tube 34 encloses the sensor element 12, the inner tube 42, and the connector 24, and a plurality of lead wires 54 connected to the connector 24 are drawn outside from the rear end of the outer tube 34. The lead wires 54 electrically conduct through the connector 24 to electrodes of the sensor element 12 (which will be described later). The gap between the outer tube 34 and the lead wires 54 is sealed by an elastic insulating member 56 made of grommet or the like. The space 50 in the outer tube 34 is filled with a reference gas (the atmospheric air in this embodiment). The rear end of the sensor element 12 is disposed within this space 50.

Figure 2:
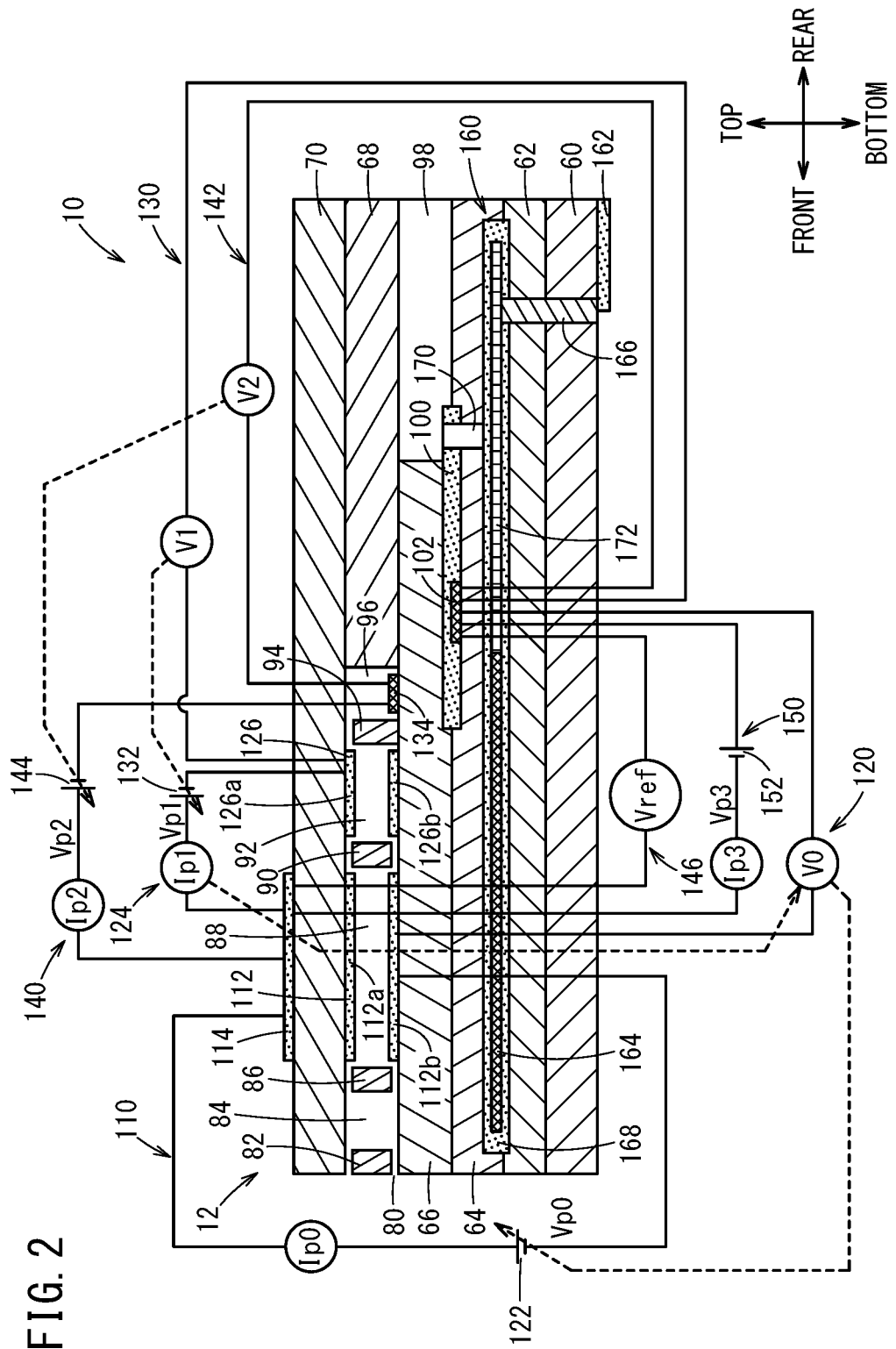
FIG. 2 is a schematic cross section schematically showing an exemplary configuration of a sensor element.

On the other hand, as shown in FIG. 2, the sensor element 12 is a device formed of a laminate in which six layers, that is, a first substrate layer 60, a second substrate layer 62, a third substrate layer 64, a first solid electrolyte layer 66, a spacer layer 68, and a second solid electrolyte layer 70 are laminated in this order from the bottom in the drawing, the six layers being each formed of an oxygen ion conducting solid electrolyte layer, such as zirconia ($ZrO_2$), for example. In addition, the solid electrolyte forming the six layers is dense and gas-tight. The sensor element 12 is produced, for example, by applying given processing to, and printing circuit patterns on, ceramic green sheets corresponding to the individual layers, laminating these sheets together, and then integrating the sheets by sintering.

Between the lower surface of the second solid electrolyte layer 70 and the upper surface of the first solid electrolyte layer 66, on the side of one end of the sensor element 12 (on the left side in FIG. 2), a gas inlet 80, a first diffusion control portion 82, a buffer space 84, a second diffusion control portion 86, a first internal chamber 88, a third diffusion control portion 90, a second internal chamber 92, a fourth diffusion control portion 94, and a third internal chamber 96 are formed in such a manner as to communicate and adjoin in this order.

The gas inlet 80, the buffer space 84, the first internal chamber 88, the second internal chamber 92, and the third internal chamber 96 are formed by hollowing out the spacer layer 68, and they are spaces in the sensor element 12 that are sectioned by the lower surface of the second solid electrolyte layer 70 at the top, the upper surface of the first solid electrolyte layer 66 at the bottom, and the main surfaces of the spacer layer 68 on the sides.

The first diffusion control portion 82, the second diffusion control portion 86, and the third diffusion control portion 90 are each formed as two oblong slits (the openings thereof have their longitudinal direction in the direction perpendicular to the drawing sheet). The fourth diffusion control portion 94 is formed as one oblong slit (the opening thereof has its longitudinal direction in the direction perpendicular to the drawing sheet) under the lower surface of the second solid electrolyte layer 70. The section from the gas inlet 80 to the third internal chamber 96 will be referred to also as a measured gas passage.

A reference gas introduction space 98 is provided in a position farther from the above-mentioned one end, than the measured gas passage. The reference gas introduction space 98 is formed between the upper surface of the third substrate layer 64 and the lower surface of the spacer layer 68 and is sectioned by a side surface of the first solid electrolyte layer 66 on the side. A reference gas for the measurement of NOx concentration, e.g., the atmospheric air (the atmosphere within the space 50 in FIG. 1), is introduced into the reference gas introduction space 98.

An atmosphere introduction layer 100 is a layer made of ceramic such as porous alumina etc. and is exposed in the reference gas introduction space 98. The reference gas is introduced to the atmosphere introduction layer 100 through the reference gas introduction space 98. The atmosphere introduction layer 100 is formed so as to cover a reference electrode 102. The atmosphere introduction layer 100 guides the reference gas in the reference gas introduction space 98 to the reference electrode 102 while providing given diffusion resistance to the reference gas. The atmosphere introduction layer 100 is formed so as to be exposed in the reference gas introduction space 98 only on the side that is further toward the rear end side of the sensor element 12 than the reference electrode 102 (on the right side in FIG. 2). In other words, the reference gas introduction space 98 is not formed to a position right above the reference electrode 102. However, the reference electrode 102 may be formed right under the reference gas introduction space 98 in FIG. 2.

The reference electrode 102 is an electrode that is formed between the upper surface of the third substrate layer 64 and the first solid electrolyte layer 66, and, as mentioned above, the atmosphere introduction layer 100 connecting to the reference gas introduction space 98 is provided around the reference electrode 102. The reference electrode 102 is formed directly on the upper surface of the third substrate layer 64 and is covered by the atmosphere introduction layer 100 except for the part contacting the upper surface of the third substrate layer 64. Also, as will be described later, it is possible to measure the oxygen concentrations (oxygen partial pressures) in the first internal chamber 88, the second internal chamber 92, and the third internal chamber 96, by using the reference electrode 102. The reference electrode 102 is formed as a porous cermet electrode (e.g., a cermet electrode of Pt and $ZrO_2$).

In the measured gas passage, the gas inlet 80 is opened to the outside space, and the measured gas is taken into the sensor element 12 from the outside space through the gas inlet 80. The first diffusion control portion 82 is a portion that provides given diffusion resistance to the measured gas taken from the gas inlet 80. The buffer space 84 is a space that guides the measured gas introduced from the first diffusion control portion 82 to the second diffusion control portion 86.

The second diffusion control portion 86 is a portion that provides given diffusion resistance to the measured gas introduced from the buffer space 84 into the first internal chamber 88. When the measured gas is introduced from the outside of the sensor element 12 into the first internal chamber 88, the measured gas rapidly taken into the sensor element 12 from the gas inlet 80 due to pressure fluctuation of the measured gas in the outside space (the pressure fluctuation can be exhaust pressure pulsation if the measured gas is an automotive exhaust gas) is not directly introduced into the first internal chamber 88, but is introduced into the first internal chamber 88 after concentration variation of the measured gas is cancelled through the first diffusion control portion 82, the buffer space 84, and the second diffusion control portion 86.

Accordingly, the concentration variation of the measured gas introduced into the first internal chamber 88 has become almost negligible. The first internal chamber 88 is provided as a space for adjusting the oxygen partial pressure in the measured gas introduced through the second diffusion control portion 86. The oxygen partial pressure is adjusted by operation of a main pump cell 110 described next.

The main pump cell 110 is an electrochemical pump cell formed of an inside pumping electrode 112 provided on the internal surfaces of the first internal chamber 88, an outside pumping electrode 114 formed on the upper surface of the second solid electrolyte layer 70 in an area corresponding to the inside pumping electrode 112 so as to be exposed to the outside space (the sensor element cavity 28 in FIG. 1), and the second solid electrolyte layer 70 sandwiched between these pumping electrodes.

The inside pumping electrode 112 is formed on the upper and lower solid electrolyte layers (the second solid electrolyte layer 70 and the first solid electrolyte layer 66) that section the first internal chamber 88, and on the spacer layer 68 that forms the side walls of the first internal chamber 88. Specifically, a ceiling electrode portion 112a of the inside pumping electrode 112 is formed on the lower surface of the second solid electrolyte layer 70 forming the ceiling surface of the first internal chamber 88, a bottom electrode portion 112b is formed directly on the upper surface of the first solid electrolyte layer 66 forming the bottom surface of the first internal chamber 88, and side electrode portions (not shown) are formed on the side wall surfaces (internal surfaces) of the spacer layer 68 forming both side walls of the first internal chamber 88, where the side electrode portions connect the ceiling electrode portion 112a and the bottom electrode portion 112b. That is, the inside pumping electrode 112 is formed as a structure like a tunnel in the part where the side electrode portions are disposed.

The inside pumping electrode 112 and the outside pumping electrode 114 are formed as porous cermet electrodes (e.g., cermet electrodes of Pt and $ZrO_2$ containing 1% Au). The inside pumping electrode 112 that contacts the measured gas is formed using a material having a weakened reduction ability for NOx components in the measured gas.

In the main pump cell 110, a desired pumping voltage Vp0 is applied across the inside pumping electrode 112 and the outside pumping electrode 114 to cause a pumping current Ip0 to flow in the positive direction or negative direction between the inside pumping electrode 112 and the outside pumping electrode 114, which enables the main pump cell 110 to pump out the oxygen in the first internal chamber 88 to the outside space, or to pump the oxygen in the outside space into the first internal chamber 88.

Further, in order to detect the oxygen concentration (oxygen partial pressure) in the atmosphere in the first internal chamber 88, a main-pump-controlling oxygen-partial-pressure-detecting sensor cell 120, which is an electrochemical sensor cell, is formed of the inside pumping electrode 112, the second solid electrolyte layer 70, the spacer layer 68, the first solid electrolyte layer 66, and the reference electrode 102.

The oxygen concentration (oxygen partial pressure) in the first internal chamber 88 is known by measuring an electromotive force V0 in the main-pump-controlling oxygen-partial-pressure-detecting sensor cell 120. Further, the pumping current Ip0 is controlled by feedback-controlling the pumping voltage Vp0 of a variable power supply 122 so as to keep the electromotive force V0 constant. The oxygen concentration in the first internal chamber 88 can thus be maintained at a certain constant value.

The third diffusion control portion 90 is a portion that provides given diffusion resistance to the measured gas whose oxygen concentration (oxygen partial pressure) has been controlled by the operation of the main pump cell 110 in the first internal chamber 88, and the third diffusion control portion 90 guides the measured gas into the second internal chamber 92.

The second internal chamber 92 is provided as a space in which the measured gas, which has undergone oxygen concentration (oxygen partial pressure) adjustment in the first internal chamber 88 in advance and is then introduced through the third diffusion control portion 90, is subjected to further oxygen partial pressure adjustment by an auxiliary pump cell 124. The oxygen concentration in the second internal chamber 92 can thus be kept constant highly accurately, enabling the gas sensor 10 to perform highly accurate NOx concentration measurement.

The auxiliary pump cell 124 is an auxiliary electrochemical pump cell including an auxiliary pumping electrode 126 provided on the inner surfaces of the second internal chamber 92, the outside pumping electrode 114 (not limited to the outside pumping electrode 114 but can be another appropriate electrode outside of the sensor element 12), and the second solid electrolyte layer 70.

The auxiliary pumping electrode 126 has a tunnel-like structure similar to that of the inside pumping electrode 112 provided in the first internal chamber 88, and is disposed in the second internal chamber 92. That is, a ceiling electrode portion 126a is formed on the second solid electrolyte layer 70 forming the ceiling surface of the second internal chamber 92, a bottom electrode portion 126b is formed directly on the upper surface of the first solid electrolyte layer 66 forming the bottom surface of the second internal chamber 92, and side electrode portions (not shown) connecting the ceiling electrode portion 126a and the bottom electrode portion 126b are formed on both wall surfaces of the spacer layer 68 forming the side walls of the second internal chamber 92, thus forming a tunnel-like structure. Similarly to the inside pumping electrode 112, the auxiliary pumping electrode 126 is also formed using a material having a weakened reduction ability for NOx components in the measured gas.

In the auxiliary pump cell 124, a desired voltage Vp1 is applied across the auxiliary pumping electrode 126 and the outside pumping electrode 114, which enables the auxiliary pump cell 124 to pump out the oxygen in the atmosphere in the second internal chamber 92 to the outside space, or to pump oxygen into the second internal chamber 92 from the outside space.

Further, in order to control the oxygen partial pressure in the atmosphere in the second internal chamber 92, an auxiliary-pump-controlling oxygen-partial-pressure-detecting sensor cell 130, which is an electrochemical sensor cell, is formed of the auxiliary pumping electrode 126, the reference electrode 102, the second solid electrolyte layer 70, the spacer layer 68, and the first solid electrolyte layer 66.

The auxiliary pump cell 124 performs pumping with a variable power supply 132 that is voltage-controlled based on an electromotive force V1 detected by the auxiliary-pump-controlling oxygen-partial-pressure-detecting sensor cell 130. Thus, the oxygen partial pressure in the atmosphere in the second internal chamber 92 can be controlled to such low partial pressure as not to substantially affect the measurement of NOx.

In addition, a pumping current Ip1 thereof is used to control the electromotive force V0 of the main-pump-controlling oxygen-partial-pressure-detecting sensor cell 120. Specifically, the pumping current Ip1 is input as a control signal to the main-pump-controlling oxygen-partial-pressure-detecting sensor cell 120 to thereby control the electromotive force V0, whereby a control is provided so that the gradient of oxygen partial pressure in the measured gas introduced from the third diffusion control portion 90 into the second internal chamber 92 can always be kept constant. When the gas sensor is used as a NOx sensor, the main pump cell 110 and the auxiliary pump cell 124 operate to keep the oxygen concentration in the second internal chamber 92 at a constant value around about 0.001 ppm.

The fourth diffusion control portion 94 is a portion that provides given diffusion resistance to the measured gas whose oxygen concentration (oxygen partial pressure) has been controlled by the operation of the auxiliary pump cell 124 in the second internal chamber 92, and the fourth diffusion control portion 94 guides the measured gas into the third internal chamber 96. The fourth diffusion control portion 94 serves to limit the amount of NOx flowing into the third internal chamber 96.

The third internal chamber 96 is provided as a space for performing processing to measure nitrogen oxide (NOx) concentration in the measured gas, which has undergone oxygen concentration (oxygen partial pressure) adjustment in the second internal chamber 92 in advance and is then introduced through the fourth diffusion control portion 94. The measurement of NOx concentration is mainly performed in the third internal chamber 96 by operation of a measurement pump cell 140.

The measurement pump cell 140 measures the NOx concentration in the measured gas in the third internal chamber 96. The measurement pump cell 140 is an electrochemical pump cell formed of a measurement electrode 134 formed directly on the upper surface of the first solid electrolyte layer 66 facing the third internal chamber 96, the outside pumping electrode 114, the second solid electrolyte layer 70, the spacer layer 68, and the first solid electrolyte layer 66. The measurement electrode 134 is a porous cermet electrode. The measurement electrode 134 functions also as a NOx reduction catalyst that reduces the NOx present in the atmosphere in the third internal chamber 96.

In the measurement pump cell 140, the oxygen generated by the decomposition of nitrogen oxide in the atmosphere around the measurement electrode 134 is pumped out, and the amount thereof can be detected as a pumping current Ip2.

Further, in order to detect the oxygen partial pressure around the measurement electrode 134, a measurement-pump-controlling oxygen-partial-pressure-detecting sensor cell 142, which is an electrochemical sensor cell, is formed of the first solid electrolyte layer 66, the measurement electrode 134, and the reference electrode 102. A variable power supply 144 is controlled based on an electromotive force V2 detected by the measurement-pump-controlling oxygen-partial-pressure-detecting sensor cell 142.

The measured gas guided into the second internal chamber 92 reaches the measurement electrode 134 in the third internal chamber 96 through the fourth diffusion control portion 94 in a state where oxygen partial pressure is controlled. The nitrogen oxide in the measured gas around the measurement electrode 134 is reduced to generate oxygen ($2NO \rightarrow N_2 + O_2$). Then, the oxygen thus generated is pumped by the measurement pump cell 140. In this process, a voltage Vp2 of the variable power supply 144 is controlled so that the electromotive force V2 detected by the measurement-pump-controlling oxygen-partial-pressure-detecting sensor cell 142 is kept constant. The amount of oxygen generated around the measurement electrode 134 is proportional to the concentration of the nitrogen oxide in the measured gas, and therefore the nitrogen oxide concentration in the measured gas is calculated using the pumping current Ip2 of the measurement pump cell 140.

Further, an electrochemical sensor cell 146 is formed of the second solid electrolyte layer 70, the spacer layer 68, the first solid electrolyte layer 66, the third substrate layer 64, the outside pumping electrode 114, and the reference electrode 102, and the oxygen partial pressure in the measured gas outside of the sensor can be detected by an electromotive force Vref obtained by the sensor cell 146. Further, an electrochemical reference-gas-adjustment pump cell 150 is formed of the second solid electrolyte layer 70, the spacer layer 68, the first solid electrolyte layer 66, the third substrate layer 64, the outside pumping electrode 114, and the reference electrode 102. The reference-gas-adjustment pump cell 150 performs pumping as a voltage Vp3 applied by a variable power supply 152 connected between the outside pumping electrode 114 and the reference electrode 102 causes a control current Ip3 to flow. The reference-gas-adjustment pump cell 150 thus pumps oxygen into the space (atmosphere introduction layer 100) around the reference electrode 102 from the space (the sensor element cavity 28 in FIG. 1) around the outside pumping electrode 114. The voltage Vp3 of the variable power supply 152 is determined in advance as a direct-current voltage such that the control current Ip3 becomes a given value (a dc current with a constant value).

In the gas sensor 10 constructed as described above, the main pump cell 110 and the auxiliary pump cell 124 are operated so that the measurement pump cell 140 is supplied with the measured gas in which the oxygen partial pressure is always kept at a constant low value (a value that does not substantially affect the NOx measurement). Thus, the NOx concentration in the measured gas can be known based on the pumping current Ip2 that flows in substantially proportion to the NOx concentration in the measured gas as the oxygen generated by NOx reduction is pumped out by the measurement pump cell 140.

In order to enhance the oxygen ion conductivity of the solid electrolyte, the sensor element 12 further includes a heater unit 160 that serves as a temperature controller which heats the sensor element 12 and keeps the temperature. The heater unit 160 includes a heater connector electrode 162, a heater 164, a through hole 166, a heater insulating layer 168, a pressure diffusion hole 170, and a lead wire 172.

The heater connector electrode 162 is an electrode that is formed in contact with the lower surface of the first substrate layer 60. The heater connector electrode 162 is connected to an external power supply to supply electricity to the heater unit 160 from outside.

The heater 164 is an electric resistor that is sandwiched from above and below between the second substrate layer 62 and the third substrate layer 64. The heater 164 is connected to the heater connector electrode 162 through the lead wire 172 and the through hole 166, where the heater 164 generates heat by being supplied with electricity from outside through the heater connector electrode 162, thereby heating the solid electrolyte forming the sensor element 12 and keeping the temperature.

Further, the heater 164 is buried in the entire area from the first internal chamber 88 to the third internal chamber 96, so that the entire sensor element 12 can be adjusted to temperatures at which the solid electrolyte is activated.

The heater insulating layer 168 is an insulating layer formed on the upper and lower surfaces of the heater 164, and made of porous alumina formed of an insulator of alumina, etc. The heater insulating layer 168 is formed for the purpose of obtaining electric insulation between the second substrate layer 62 and the heater 164 and electric insulation between the third substrate layer 64 and the heater 164.

The pressure diffusion hole 170 passes through the third substrate layer 64 to communicate with the reference gas introduction space 98, in order to reduce internal pressure increase caused by temperature rise in the heater insulating layer 168.

The variable power supplies 122, 144, 132, 152, etc. shown in FIG. 2 are connected to electrodes through lead wires (not shown) actually formed in the sensor element 12 and the connector 24 and lead wires 54 in FIG. 1.

Now, as shown in FIG. 1, in this embodiment, the terminal members 18 extending rearward are electrically connected to corresponding element pads 200 that are exposed from the rear end portion of the sensor element 12. The ceramic housing 16 is provided around the rear end portion of the sensor element 12, and the terminal members 18 are fitted between the element pads 200 and the ceramic housing 16, whereby the element pads 200 of the sensor element 12 and the terminal members 18 are press fitted and electrically connected together. That is, the ceramic housing 16 is attached with the terminal members 18 electrically connected to the sensor element 12 and holds the rear end portion of the sensor element 12.

The rear ends of the terminal members 18 extend rearward behind the ceramic housing 16 and are electrically connected by solder or the like to the lead wires 54 inserted in the elastic insulating member 56. The elastic insulating member 56 has formed therein a plurality of through holes 202 along the axial direction of the sensor element 12. The lead wires 54 are inserted through the through holes 202, and the terminal members 18 extending from the sensor element 12 and the lead wires 54 are electrically connected by solder or the like.

In this embodiment, an end surface 46a of the sealing material 46 is inclined with respect to the main surfaces 12a, 12b of the sensor element 12. That is, an angle of inclination, θ1, which is described later, is not 90° (not perpendicular).

FIGS. 3A to 3C, 4A and 4B, 5A to 5C, 6A and 6B, 7A and 7B, and 8A and 8B show the sealing material 46 and the sensor element 12 cut along a reference plane S0.

Figure 9:
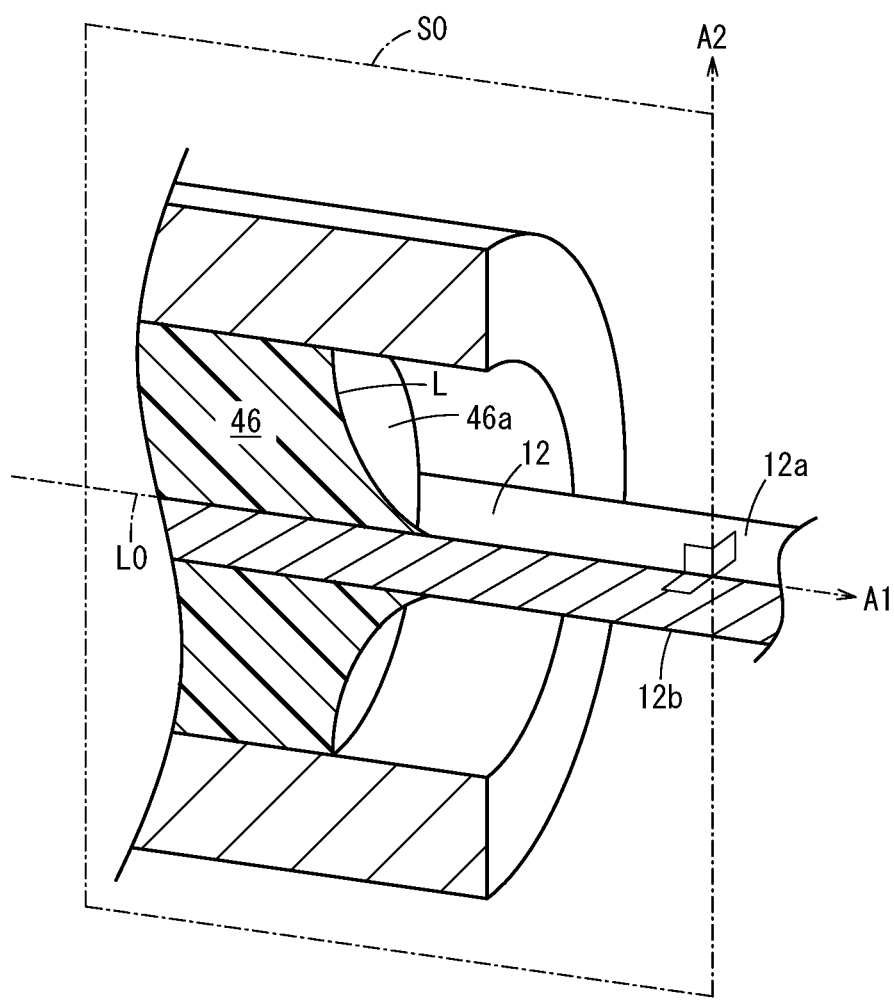
FIG. 9 is a perspective view schematically illustrating a reference plane.

As shown in FIG. 9, the reference plane S0 can be defined as a plane that includes an axis A1 along the front-rear direction of the sensor element 12 (a first direction: the direction in which the sensor element 12 extends) and an axis A2 along its top-bottom direction (a third direction: a direction that is perpendicular to the main surfaces 12a, 12b of the sensor element 12).

In this embodiment, the main surfaces 12a, 12b are surfaces that face in opposite directions to each other (surfaces facing in opposite directions differing by 180°), and the reference plane S0 is common to the main surfaces 12a, 12b. If the main surfaces 12a, 12b are not directed in the opposite directions (if they are positioned obliquely to each other), then it is necessary to define separate reference planes S0 respectively for the main surfaces 12a, 12b.

Now, the main surfaces 12a and 12b are assumed to be facing in the opposite directions and the inclination angles θ1 and θ2 (first and second inclination angles) will be described mainly about the structure on the side of the main surface 12a. The description about the structure on the main surface 12a applies also to the structure on the main surface 12b.

The end surface 46a of the sealing material 46 intersects the reference plane S0 to define a line segment L (an edge of the end surface 46a). Further, the main surface 12a of the sensor element 12 intersects the reference plane S0 to define a reference line L0 (an edge of the end surface 46a). The inclination angle θ1 is the angle between the line segment L and the reference line L0 (in essence, the angle that the end surface 46a of the sealing material 46 forms with the main surface 12a of the sensor element 12).

In FIGS. 3A to 3C and FIGS. 4A and 4B, this line segment L (see FIG. 9) is formed of a single straight line or a plurality of straight lines. In FIGS. 5A to 5C and FIGS. 6A and 6B, this line segment L is formed of a single curved line or a plurality of curved lines. In FIGS. 7A and 7B and FIGS. 8A and 8B, this line segment L is formed of a combination of straight and curved lines.

Figure 3A:
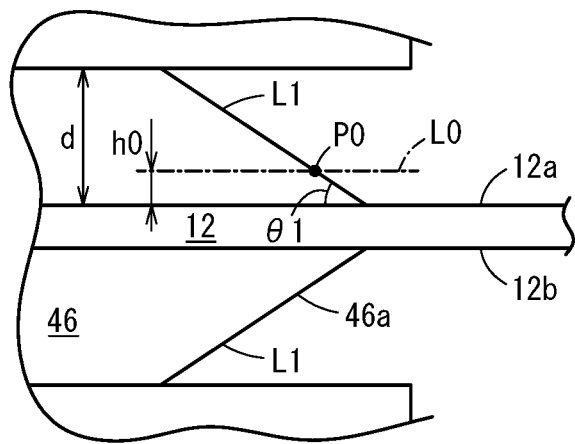
FIGS. 3A, 3B, and 3C are cross sections schematically showing an end of a sealing material and its vicinity.
Figure 5A:
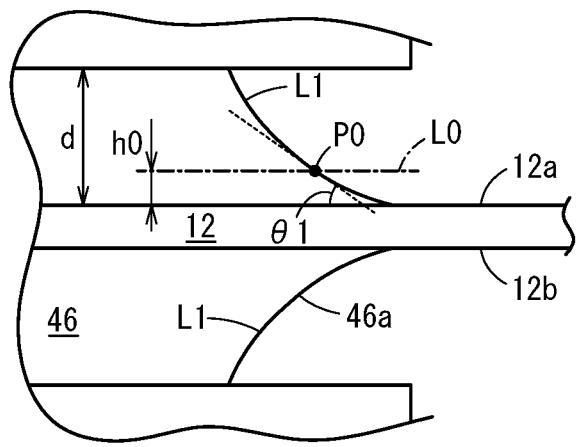
FIGS. 5A, 5B, and 5C are cross sections schematically showing an end of a sealing material and its vicinity.

In FIGS. 3A and 5A, the line segment L is formed of a single straight line L1 or curved line L1, which is inclined at the inclination angle θ1 with respect to the reference line L0 (the main surface (surface) 12a of the sensor element 12).

Now, a point of intersection P0 between the line segment L and a plane spaced by a reference height h0 from the main surface 12a of the sensor element 12 is defined (which will hereinafter be referred to as reference point P0). The reference height h0 is a height corresponding to a quarter of a thickness d of the sealing material 46 (h0=d/4), for example. This reference point P0 is the point of reference for the inclination angle θ1, and the gradient of the line segment L at the reference point P0 (the gradient of the tangent line to the line segment L, or, in essence, the gradient of the tangent plane to the end surface 46a at the reference point P0) defines the inclination angle θ1.

As shown in FIG. 3A, if the line segment L is a single straight line, it is not necessary to pay attention to the reference point P0. The reference point P0 effectively functions if the line segment L is a curved line or includes a plurality of lines (straight and/or curved lines).

In this way, the inclination angle θ1 can be defined as the gradient of the line L1 at the reference point P0 with respect to the reference line L0 (if the line L1 is a curved line, then it is the gradient of the tangent line to the line L1 at the reference point P0). This definition applies irrespective of whether the line L1 is a straight line or curved line.

The inclination angle θ1 is preferably not less than 10° and not more than 80°, and more preferably not more than 70°. By setting the inclination angle θ1 to be smaller than 90° (so that the sealing material 46 obliquely contacts the sensor element 12), it is possible to disperse the stress of an impact on the gas sensor 10 in the longitudinal (front-rear) direction of the sensor element 12 so as to reduce the stress in the vertical direction of the sensor element 12. This, as a result, prevents breakage and the like of the sensor element 12 when subjected to an impact.

The line segment L may include a plurality of lines (the end surface 46a may include a plurality of surfaces divided by a boundary or boundaries). In this case, the end surface 46a can be divided into a first surface and a second surface on either side of the boundary. The first surface is in contact with the main surface 12a and the second surface is spaced at a distance from the main surface 12a.

Figure 3B:
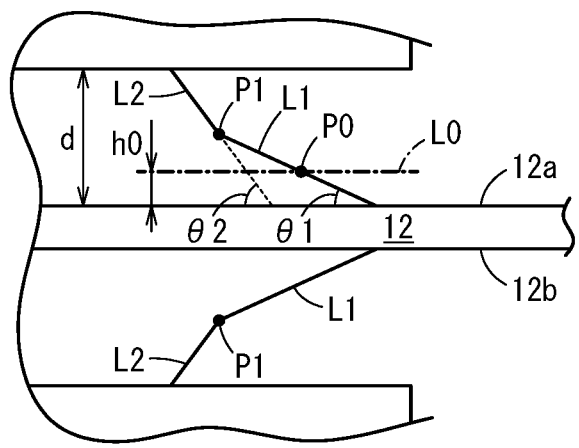
Figure 5B:
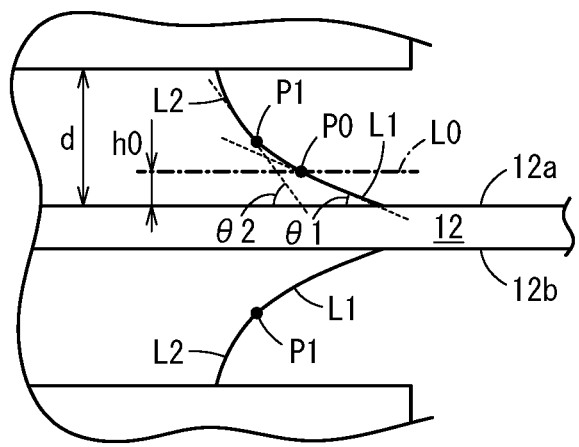

In this case, in FIGS. 3B and 5B, the line segment L includes lines L1 and L2 (in essence, two surfaces) and a boundary point P1 connecting the lines (in essence, a boundary between the two surfaces). That is, in FIG. 3B, the straight lines L1 and L2 with different gradients are connected at the boundary point P1. In FIG. 5B, the curved lines L1 and L2 are connected at the boundary point P1 and the gradients of the curved lines L1 and L2 at this boundary point P1 (the gradients of the tangent lines to the curved lines L1 and L2) differ from each other. That is, the gradient of the line segment L (the tangent planes to the end surface 46a) at the boundary point P1 is discontinuous.

In this way, if the line segment L has the boundary point P1, the relation with the reference point P0 becomes an issue. It is assumed here that the boundary point P1 is outside (above) the reference point P0. Then, the line segment L has an inclination angle $\theta 2$ in addition to the inclination angle $\theta 1$.

The inclination angle $\theta 2$ can be defined as the gradient of the line L2 at the boundary point P1 with respect to the reference line L0 (the gradient of the tangent line to the line L2, or, in essence, the gradient of the tangent plane to the end surface 46a (see FIG. 9)).

Even if there are inclination angles $\theta 1$ and $02$ in this way, the inclination angle $\theta 1$ is preferably not less than 10° and not more than 80°, and more preferably not more than 70°.

It is also preferred that the inclination angle $\theta 1$ is smaller than the inclination angle $\theta 2$ ($\theta 1<\theta 2$). In this case, the angle (inclination angle $\theta 1$) between the main surface 12a of the sensor element 12 and the sealing material 46 will be still smaller and breakage of the sensor element 12 and the sealing material 46 can be reduced easily. On the other hand, if $\theta 1$ is larger than $\theta 2$ ($\theta 1>\theta 2$), the angle (inclination angle $\theta 1$) with respect to the sensor element 12 will be larger, leading to excessive stress concentration at the boundary point P and hence to breakage of the sealing material 46.

Figure 3C:
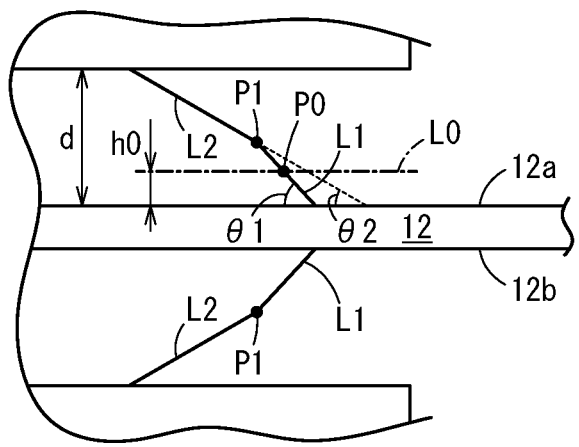
Figure 5C:
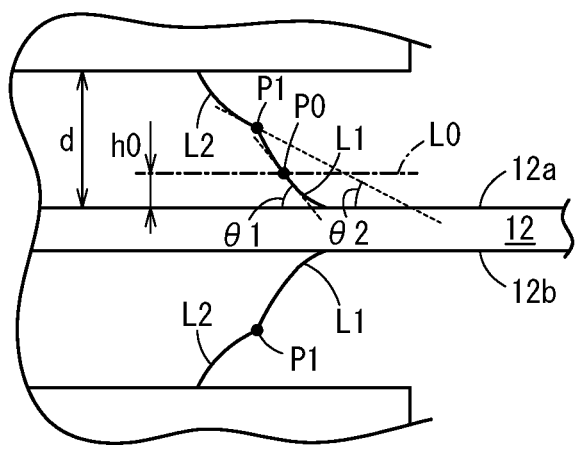

FIGS. 3C and 5C show examples in which the inclination angle $\theta 1$ is larger than the inclination angle $\theta 2$.

Figure 4A:
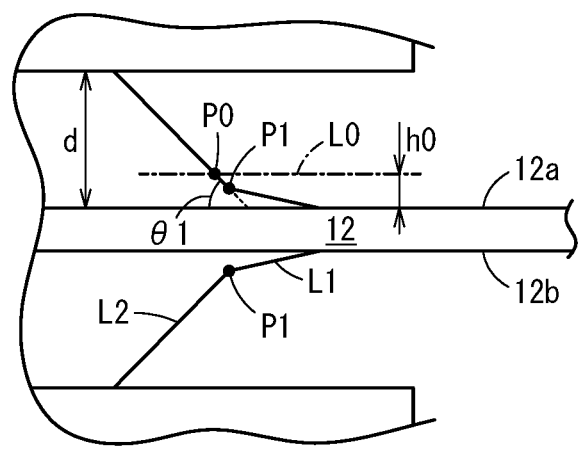
FIGS. 4A and 4B are cross sections schematically showing an end of a sealing material and its vicinity.
Figure 6A:
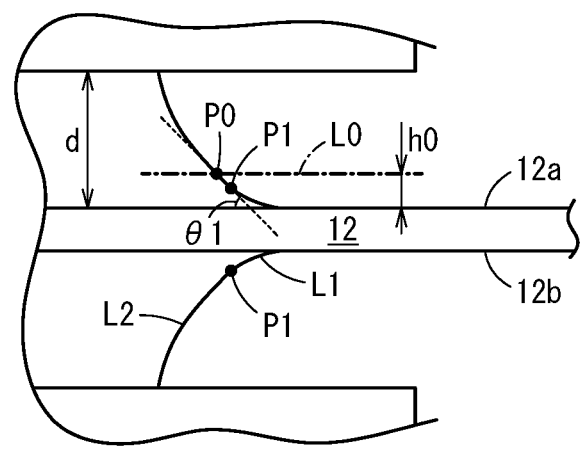
FIGS. 6A and 6B are cross sections schematically showing an end of a sealing material and its vicinity.

In FIGS. 4A and 6A, the boundary point P1 resides inside the reference point P0. In this case, the inclination angle $\theta 1$ is defined as the gradient of the line L2 at the reference point P0 with respect to the reference line L0. That is, a boundary point within the reference height h0 is ignored when considering the inclination angle $\theta 1$. In this case, the inclination angle $\theta 2$ is not defined.

Figure 4B:
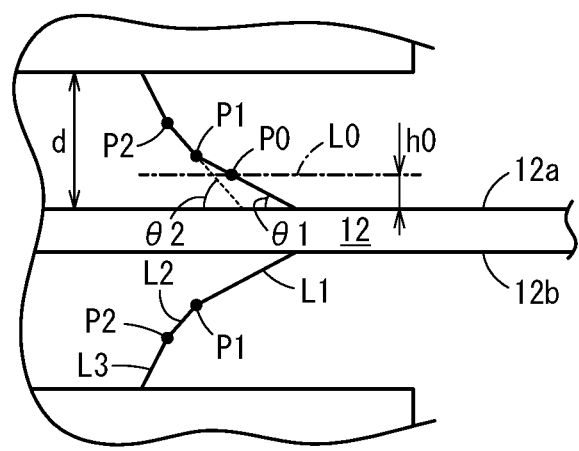
Figure 6B:
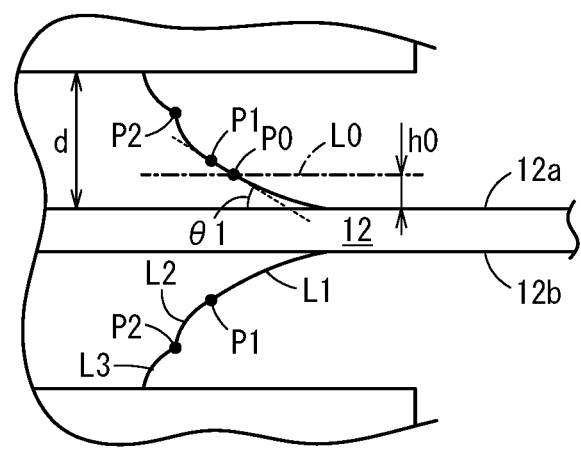

Now, two, or three or more boundary points P may exist. FIGS. 4B and 6B show examples in which there are three lines L1 to L3 and two boundary points P1 and P2. The straight lines L1 and L2 are connected to each other at the boundary point P1, and the straight lines L2 and L3 are connected to each other at the boundary point P2. FIGS. 4B and 6B show examples in which the boundary point P1 is located outside of the reference point P0. As a result, the inclination angles $\theta 1$ and $\theta 2$ corresponding to the straight lines L1 and L2 are determined. If the boundary point P1 is located inside the reference point P0, then the inclination angles $\theta 1$ and $\theta 2$ corresponding to the straight lines L2 and L3 are determined.

Figure 7A:
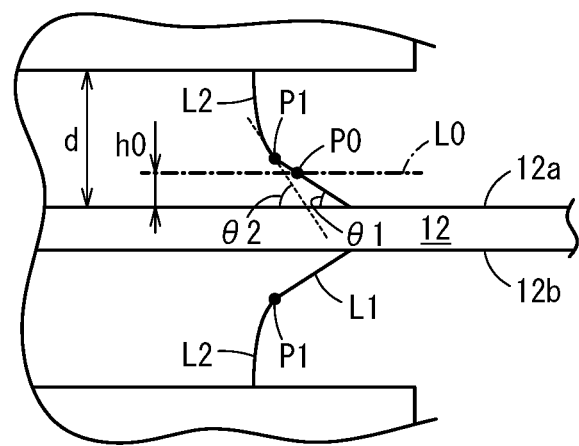
FIGS. 7A and 7B are cross sections schematically showing an end of a sealing material and its vicinity.
Figure 7B:
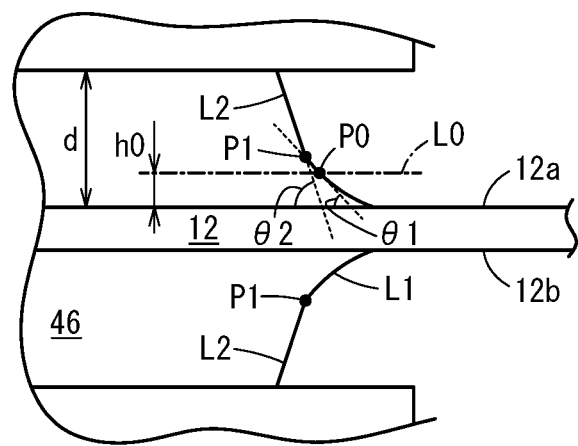
Figure 8A:
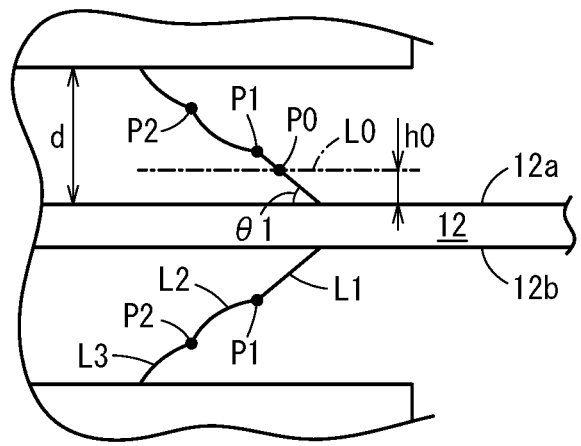
FIGS. 8A and 8B are cross sections schematically showing an end of a sealing material and its vicinity.
Figure 8B:
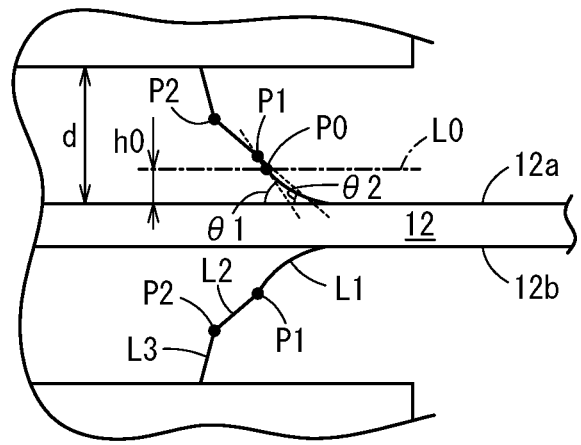

The line segment L described above includes straight line(s) or curved line(s) only. The line segment L may be formed of a combination of straight and curved lines. In FIGS. 7A and 7B, the lines L1 and L2 forming the line segment L are a combination of a straight line and a curved line and a combination of a curved line and a straight line, respectively. In FIGS. 8A and 8B, the lines L1, L2, L3 forming the line segment L are a combination of a straight line, a curved line, and a curved line, and a combination of a curved line, a straight line, and a straight line, respectively. In this way, the lines L1 to L3 can be straight or curved.

In the embodiment above, the inner tube 42 is filled with the sealing material 46. In this configuration, the sealing material 46 is in direct contact with the main fitting 40 and the inner tube 42.

The sealing material 46 may be formed of a combination of a plurality of members. For example, ceramic supporters and powder compacts may be arranged alternately to form the sealing material 46. In this case, it is sufficient that at least one member has an inclination angle $\theta 1$ of not less than 10° and not more than 80° with respect to the sensor element 12. Thus, even when a plurality of members are combined to form the sealing material 46, breakage and the like of the sensor element 12 can be reduced by setting the inclination angle $\theta 1$ of one member to be not less than 10° and not more than 80°.

EXAMPLES

Now, an example experiment will be described. In this experiment, the sensor element 12 was subjected to impact resistance testing to check the presence or absence of chipping, breakage, and conduction, with different values of the inclination angle $\theta 1$, with different combinations of straight and curved lines forming the line segment L, and in the presence and absence of a boundary point.
(Method of Evaluation)
The testing and evaluation methods will be described below.
Test conditions: A weight (100 g) was dropped from a height of 1.5 m onto the position of the sealing material 46 of the sensor assembly 20 to apply an impact to the contact (stone impact). After this, the gas sensor 10 was disassembled and observed to see whether the sensor element 12 suffered failures such as breakage (measurement of strength).
(Evaluations)
A: Sensor element 12 was broken or not broken with five times of stone impacting.
B: Sensor element 12 was broken with three to four times of stone impacting.
C: Sensor element 12 was broken with twice or less times of stone impacting.

The condition of the end surface 46a of the sealing material 46 was classified into the four conditions (1) to (4) below.

(1) The condition of FIG. 3A (The end surface 46a forms a single straight line L1 on the reference plane S0.)

(2) The condition of FIG. 3B (The end surface 46a forms two straight lines L1 and L2 with different gradients on the reference plane S0.)

(3) The condition of FIG. 5A (The end surface 46a forms a single curved line L1 on the reference plane S0.)

(4) The condition of FIG. 5B (The end surface 46a forms two curved lines L1 and L2 on the reference plane S0, with the curved lines L1 and L2 having different gradients at the boundary point P1.)

In examples 1 to 4, examples 5 to 8, examples 9 to 12, and examples 13 to 16, the end surface 46a of the sealing material 46 had the shapes corresponding to the conditions (1) to (4) above, respectively. A comparative example 1 had the shape corresponding to the condition (1). In all of the examples 5 to 8 and examples 13 to 16 having the boundary point P1, the height of the boundary point P1 was set to be higher than the reference height h0. That is, in these cases, the inclination angle θ1 is determined by the line L1, regardless of the line L2.

In the examples 1 to 4, the inclination angle θ1 was set to 80, 70, 50, 20 [°], respectively. In the examples 5 to 8, the inclination angle θ1 was set to 80, 70, 30, 10 [°], respectively. In the examples 9 to 12, the inclination angle θ1 was set to 80, 70, 50, 20 [°], respectively. In the examples 13 to 16, the inclination angle θ1 was set to 80, 70, 30, 10 [°], respectively. In the comparative example 1, the inclination angle θ1 was set to 90 [°].

The sealing material 46 can be formed by shaping porcelain or talc or by melting and solidifying glass material. The inclination angle θ1 formed by the end surface 46a of the sealing material 46 was defined by shaping porcelain or talc in clay or powder form with a mold or jig adapted to the intended shapes, or by shaping glass material with a mold or the like.

As shown in FIG. 10, as the results of testing, the examples 1 to 16 were given ranks B, A, A, A, B, A, A, A, B, A, A, A, B, A, A, A, respectively, and the comparative example 1 was given rank C. Ranks A and B were obtained by setting the inclination angle θ1 to 10 to 80 [°]. Among them, rank A was obtained by setting the inclination angle θ1 in the range of 70 [°] or less.

As described above, the stress generated when an impact occurs can be reduced by inclining the sealing material 46 with respect to the main surfaces 12a, 12b of the sensor element 12, which reduces failures of the sensor element 12 such as breakage, so as to improve the durability.

Modification

Figure 11:
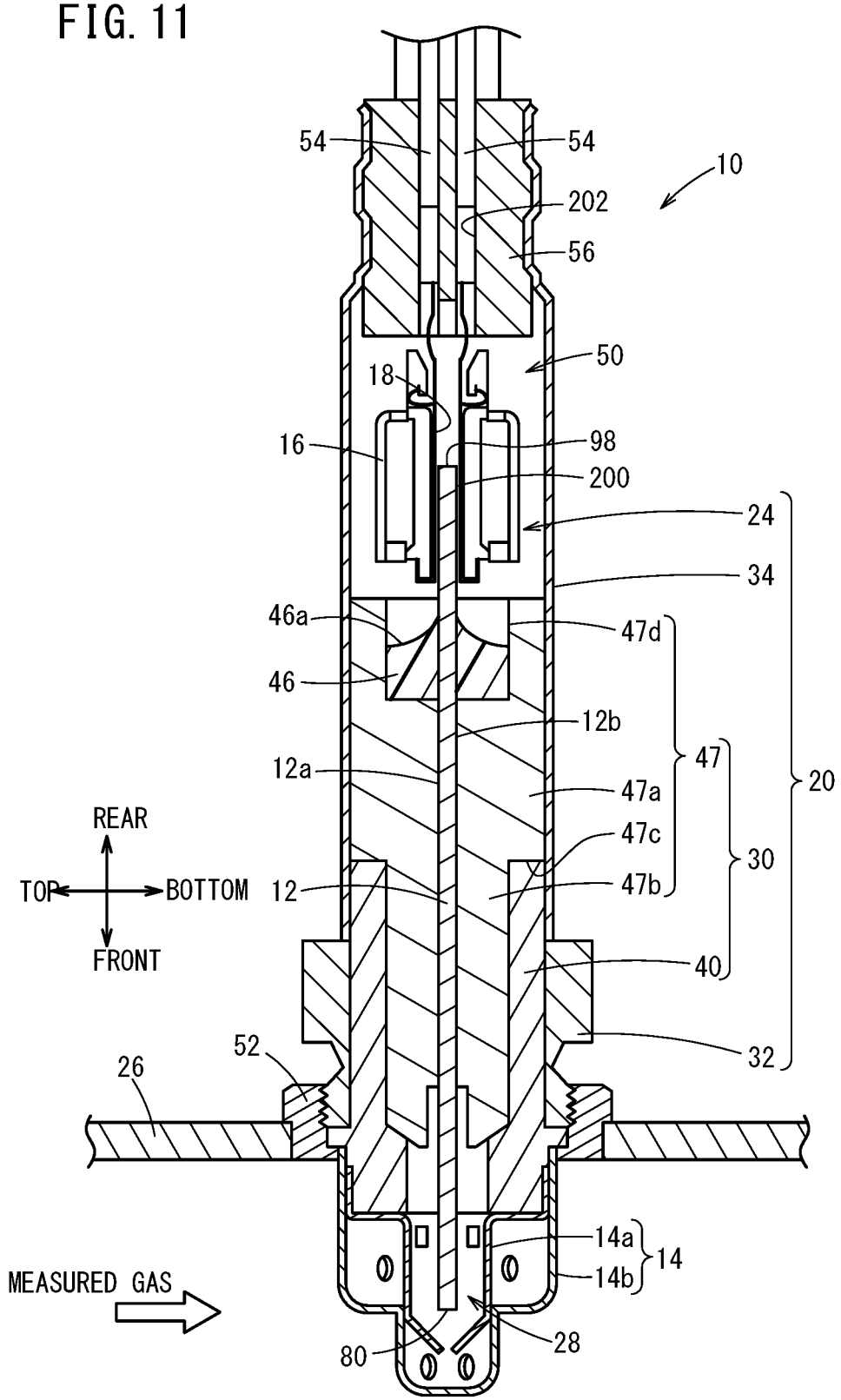
FIG. 11 is a cross section illustrating a gas sensor according to a modification.

A modification will be described below. FIG. 11 is a cross section illustrating a gas sensor 10 according to the modification.

An element seal body 30 of the modification differs from the embodiment in that it does not include the inner tube 42 but has the tubular, main fitting 40 and an insulator 47 (an example of a ceramic member) that is held within the main fitting 40 and outer tube 34 (an example of a tubular body made of metal).

The insulator 47 includes a large-diameter portion 47a, a small-diameter portion 47b, and a step portion 47c. The large-diameter portion 47a is substantially cylindrical, and is held in the outer tube 34 and has a substantially cylindrical recess 47d. The recess 47d is filled with the sealing material 46 to seal the sensor element 12. The small-diameter portion 47b is substantially cylindrical and held in the main fitting 40 and further in the outer tube 34. The step portion 47c is formed at the boundary between the large-diameter portion 47a and the small-diameter portion 47b, and is located at the rear end of the main fitting 40 in the outer tube 34. The sealing material 46 provides a seal between the sensor element cavity 28 in the protective cover 14 and the space 50 in the outer tube 34 and fixes the sensor element 12. The sealing material 46 can be formed by melting and solidifying glass material in powder or pellet form, for example.

Now, the insulator 47 has greater toughness than the sealing material 46, and the main fitting 40 has greater toughness than the insulator 47. As a result, when subjected to external stress, the insulator 47 and the sealing material 46 serve as cushioning and reduce the stress applied to the surfaces of the element.

In this modification, as in the embodiment, the stress generated when an impact occurs can be reduced by inclining the sealing material 46 with respect to the main surfaces 12a, 12b of the sensor element 12, which reduces failures of the sensor element 12 such as breakage, so as to improve the durability.

In the example above, the insulator 47 is disposed in the outer tube 34 (metal housing), and the recess 47d is filled with the sealing material 46. In this case, the sealing material 46 is not in direct contact with the outer tube 34. Alternatively, without using the insulator 47, the outer tube 34 (metal housing) may be filled with the sealing material 46. In this case, the sealing material 46 is in direct contact with the outer tube 34.

In the modification, the presence of the insulator 47 between the sealing material 46 and the outer tube 34 reduces the stress more effectively than when the sealing material 46 is in direct contact with the outer tube 34 (metal housing).

It is preferred that the insulator 47 has greater toughness than the sealing material 46 and that the outer tube 34 made of metal has greater toughness than the insulator 47. The insulator 47 and the sealing material 46 then function as cushioning and further reduce the stress applied to the surfaces of the element.

Invention Obtained from Embodiments

The invention that can be grasped from the embodiment and modification will be recited below.

[1] A gas sensor (10) according to an embodiment includes: a sensor element (12); a tubular body (42, 34) made of metal and including a through hole which is formed along an axial direction and through which the sensor element (12) is inserted; and a sealing material (46) placed inside the through hole and between an inner peripheral surface of the through hole and the sensor element (12). The sealing material (46) covers a part of a surface (12a) of the sensor element (12) and includes an end surface (46a). When the sensor element (12) is viewed in cross section from a second direction that is perpendicular to a first direction corresponding to the longitudinal direction of the sensor element (12), the end surface (46a) forms a first inclination angle (θ1) of not less than 10° and not more than 80° with respect to the surface (12a).

Then, when the gas sensor (10) undergoes an impact, it is possible to disperse the stress in the first direction (in the longitudinal direction of the sensor element 12) to reduce breakage and the like of the sensor element (12).

[2] In the embodiment, the first inclination angle (θ1) is not more than 70°. It is then possible to further disperse the stress in the first direction (the longitudinal direction of the sensor element (12)) to further reduce breakage and the like of the sensor element (12).

[3] In the embodiment, the first inclination angle (θ1) is the gradient of the end surface (46a) with respect to the surface (12a) at a reference height (h0) corresponding to a quarter of the thickness of the sealing material (46) from the surface (12a). Then, the first inclination angle (θ1) can be clearly defined even if the end surface (46a) has a curved shape.

[4] In the embodiment, the end surface (46a) includes a first surface in contact with the surface (12a), a second surface spaced apart from the surface (12*a*), and a boundary between the first and second surfaces. The first and second surfaces have different gradients at the boundary, and the height of the boundary from the surface (12*a*) is larger than the reference height (h0). The first inclination angle (θ1) is the gradient of the first surface at the reference height (h0) with respect to the surface (12*a*). Thus, the first inclination angle (θ1) can be defined clearly even if the end surface (46*a*) has first and second surfaces having different gradients at the boundary.

[5] In the embodiment, a second inclination angle (θ2) corresponding to the gradient of the second surface at the boundary with respect to the surface (12*a*) is larger than the first inclination angle (θ1). In this way, when the end surface (46*a*) has first and second inclination angles (θ1, θ2) with respect to the surface (12*a*), the second inclination angle (θ2) distant from the surface (12*a*) is set larger than the first inclination angle (θ1) closer to the surface (12*a*), whereby it is possible to prevent stress concentration at the boundary and hence breakage of the sealing material (46).

[6] In the embodiment, the surface (12*a*) is perpendicular to a third direction that is perpendicular to the first direction and the second direction. On a reference plane (S0) along the first and third directions, the first and second surfaces and the surface (12*a*) form a first line, a second line, and a third line (L1, L2, 12*a*), respectively, and a boundary point (P1) corresponding to the boundary is located between the first and second lines (L1, L2). The first inclination angle (θ1) is the gradient of the first line (L1) at the boundary point (P1) with respect to the third line (12*a*), and the second inclination angle (θ2) is the gradient of the second line (L2) at the boundary point (P1) with respect to the third line (12*a*). In this way, the reference plane (S0) is defined by the first direction in which the sensor element (12) extends and the third direction perpendicular to the surface (12*a*) thereof, and thus the first and second inclination angles (θ1, θ2) can be defined more clearly.

In the embodiment, the first and second lines (L1, L2) may be straight or curved. If the first line (L1) is a curved line, "the gradient of the first line (L1) at the boundary point (P1)" corresponds to the gradient of the tangent line to the first line (L1) at the boundary point (P1). If the second line (L2) is a curved line, "the gradient of the second line (L2) at the boundary point (P1)" corresponds to the gradient of the tangent line to the second line (L2) at the boundary point (P1).

[7] In the embodiment, a ceramic member (47) is disposed in the through hole and the ceramic member (47) includes a recess (47*d*). The sealing material (46) is placed in the recess (47*d*).

[8] In the embodiment, the ceramic member (47) has greater toughness than the sealing material (46), and the tubular body (42, 34) made of metal has greater toughness than the ceramic member (47). As a result, the ceramic member (47) and the sealing material (46) function as cushioning and further reduce the stress applied to the surface (12*a*) of the sensor element (12).

In implementation of the present invention, various means may be further provided to improve reliability as an automotive component without departing from the idea of the present invention.

What is claimed is:

1. A gas sensor comprising:
   a sensor element;
   a tubular body made of metal and including a through hole which is formed along an axial direction and through which the sensor element is inserted; and
   a sealing material placed inside the through hole of the tubular body and between an inner peripheral surface of the through hole of the tubular body and the sensor element,
   the sealing material contacting and covering a part of a surface of the sensor element and including an end surface, wherein, when the sensor element is viewed in cross section from a second direction that is perpendicular to a first direction corresponding to a longitudinal direction of the sensor element, the end surface of the sealing material forms a first inclination angle of not less than 10° and not more than 80° with respect to the surface of the sensor element.

2. The gas sensor according to claim 1, wherein the first inclination angle is not more than 70°.

3. The gas sensor according to claim 1, wherein the first inclination angle is a gradient of the end surface with respect to the surface at a reference height corresponding to a quarter of a thickness of the sealing material from the surface.

4. The gas sensor according to claim 3, wherein
   the end surface includes a first surface in contact with the surface, a second surface spaced apart from the surface, and a boundary between the first and second surfaces,
   the first and second surfaces have different gradients at the boundary,
   a height of the boundary from the surface is larger than the reference height, and
   the first inclination angle is a gradient of the first surface at the reference height with respect to the surface.

5. The gas sensor according to claim 4, wherein a second inclination angle corresponding to a gradient of the second surface at the boundary with respect to the surface is larger than the first inclination angle.

6. The gas sensor according to claim 4, wherein
   the surface is perpendicular to a third direction that is perpendicular to the first direction and the second direction,
   on a reference plane along the first and third directions, the first and second surfaces and the surface form a first line, a second line, and a third line, respectively,
   a boundary point corresponding to the boundary is located between the first and second lines,
   the first inclination angle is a gradient of the first line at the boundary point with respect to the third line, and
   the second inclination angle is a gradient of the second line at the boundary point with respect to the third line.

7. The gas sensor according to claim 1, wherein
   a ceramic member is disposed in the through hole,
   the ceramic member includes a recess, and
   the sealing material is placed in the recess.

8. The gas sensor according to claim 7, wherein
   the ceramic member has greater toughness than the sealing material, and
   the tubular body made of metal has greater toughness than the ceramic member.

* * * * *